United States Patent
Bruck

(10) Patent No.: US 7,264,081 B2
(45) Date of Patent: Sep. 4, 2007

(54) HEARING PROTECTION EARPLUG

(75) Inventor: Stefan Bruck, Nürnberg (DE)

(73) Assignee: Uvex Arbeitsschutz GmbH, Fürth (DE)

( * ) Notice: Subject to any disclaimer, the term of this patent is extended or adjusted under 35 U.S.C. 154(b) by 0 days.

(21) Appl. No.: 11/448,677

(22) Filed: Jun. 8, 2006

(65) Prior Publication Data
US 2006/0278468 A1    Dec. 14, 2006

(30) Foreign Application Priority Data
Jun. 10, 2005 (DE) .................. 20 2005 009 132 U

(51) Int. Cl.
*A61B 7/02* (2006.01)
(52) U.S. Cl. .................. 181/135; 181/129; 181/136; D24/106; D24/174
(58) Field of Classification Search ........... 181/129, 181/130, 135, 136; D24/106, 173, 174
See application file for complete search history.

(56) References Cited

U.S. PATENT DOCUMENTS

| | | | |
|---|---|---|---|
| D307,325 S * | 4/1990 | Gardner, Jr. | D24/106 |
| 5,044,463 A | 9/1991 | Carr | |
| D371,193 S * | 6/1996 | Myers et al. | D24/106 |
| D405,173 S * | 2/1999 | Falco | D24/106 |
| D419,676 S * | 1/2000 | Garcia | D24/173 |
| D481,118 S * | 10/2003 | Doty et al. | D24/106 |
| 6,981,504 B2 * | 1/2006 | Jenkins, Jr. | 128/864 |
| D524,937 S * | 7/2006 | Doty et al. | D24/106 |

FOREIGN PATENT DOCUMENTS

| | | |
|---|---|---|
| DE | 30 41 264 C2 | 5/1981 |
| WO | WO 02/43633 A1 | 6/2002 |
| WO | WO 2005/023147 A2 | 3/2005 |

\* cited by examiner

*Primary Examiner*—Michael Sherry
*Assistant Examiner*—Terrence Willoughby
(74) *Attorney, Agent, or Firm*—Browdy and Neimark, PLLC

(57) ABSTRACT

In a hearing protection earplug for insertion into the ear canal ear composed of a soft material, especially a foam material, having a cavity that is open toward the outside, it is provided, with a view to achieving additionally increased wearing comfort accompanied with easy handling during insertion into and removal from the ear, that the cavity, as seen in the cross-section, has an approximately cross-shaped configuration.

5 Claims, 1 Drawing Sheet

HEARING PROTECTION EARPLUG

BACKGROUND OF THE INVENTION

1. Field of the Invention

The invention is directed to a hearing protection earplug for insertion into the ear canal composed of a soft material, especially a foam material, having a cavity that is open toward the outside.

2. Background Art

A hearing protection earplug of this type is known from U.S. Pat. No. 5,044,463. The known longitudinal cavity is intended to increase the wearing comfort.

From WO 02/43633 A1, a hearing protection earplug is known that is provided with a handle composed of a harder, more dimensionally stable material, wherein indentations are provided at the end of the handle, for affixing a cord.

WO 2005/023147 A2, too, describes a hearing protection earplug having a main body of a soft foam material and a harder core that is intended to facilitate the insertion. An X-shaped recess at the front end serves to remove the hard end of the core to increase the wearing comfort.

SUMMARY OF THE INVENTION

With this as the starting point, the invention has as its object to improve a known hearing protection earplug according to the preamble in such a way that not only an additionally increased wearing comfort is achieved, but especially also an easy handling during the insertion into and removal from the ear.

This object is met according to the invention in such a way that the longitudinal cavity, as seen in the cross-section, has an approximately cross-shaped configuration.

As a result of the inventive configuration of the cavity, a higher degree of softness and elasticity is attained on the flat upper side or outside of the plug with the relatively hard edges that are present there, thus further increasing the wearing comfort compared with a cylindrical longitudinal cavity, because the edge as a whole becomes more pliable.

As a result of the cross-shaped configuration, the plug can be optimally compressed during the insertion, so that the insertion process is facilitated. For the removal, the plug can be grasped with one's fingernails in the region of the cavity and held securely.

An additional longitudinal cavity that extends away from the base permits a targeted adjustment of the attenuation properties, e.g., in such a way that a residual ability to hear remains despite the attenuation of the general sound level.

The invention will be explained in more detail below based on a preferred embodiment, in conjunction with the drawing.

DESCRIPTION OF A PREFERRED EMBODIMENT

Figure 1:
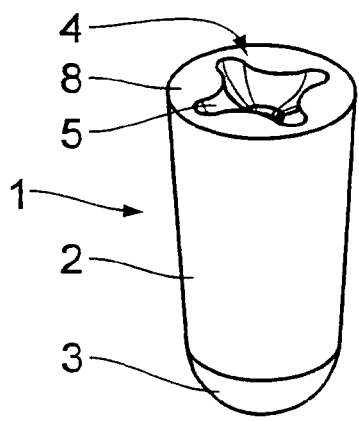
FIG. 1 shows a perspective view of an inventive hearing protection earplug at an angl from above, from above.
Figure 2:
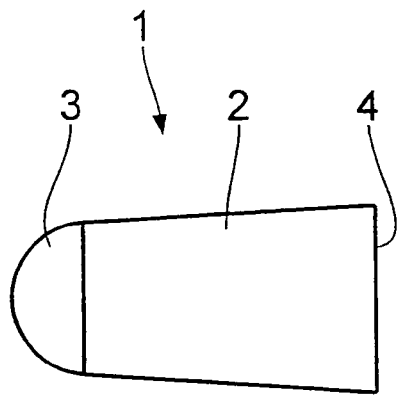
FIG. 2 shows a side view.

A hearing protection earplug 1 depicted in the drawing is composed of a slow recovery polyurethane foam and is produced by casting.

The hearing protection earplug 1 comprises a main body 2, which narrows conically toward the inside, a rounded bottom end 3, and a flat top end 4.

Figure 3:
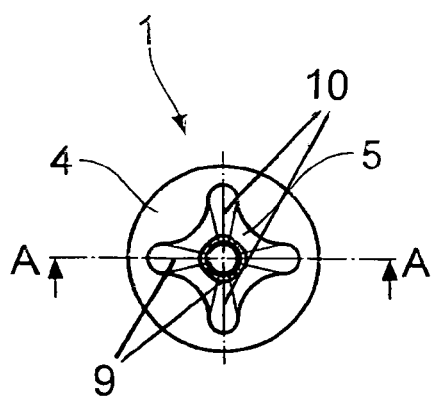
FIG. 3 shows a top view of the outer end surface.
Figure 4:
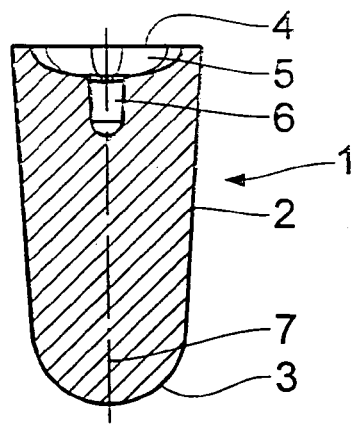
FIG. 4 shows a section along the line A-A in FIG. 3.

Provided at the flat top end 4 is a cavity 5, which has a cross-shaped basic shape formed by two intersecting channels 9, 10 with rounded transitions, as is apparent in FIG. 3.

Adjoining the relatively shallow cavity 5 is a longitudinal cavity 6, which extends along the longitudinal axis 7 of the main body 2 at the intersection of the channels 9, 10.

The cross-shaped cavity 5 serves to make the edge region 8 of the end surface at the end 4 more pliable and to that effect increase the wearing comfort. At the same time the end 4 can be compressed easily during the insertion of the plug, owing to the configuration of the cavity 5, thereby facilitating the insertion and, on the other hand, ensuring an even, defined fit in the ear after the insertion. The cavity 5 is also helpful when removing the hearing protection earplug 1, as it significantly facilitates grasping of the plug.

What is claimed is:

1. A hearing protection earplug comprising:
   a main body a soft material particularly a foam material which tapers conically from a top end of the earplug to a bottom end of the earplug;
   wherein the bottom end is formed to be inserted first into an ear canal;
   said earplug having a cavity on the top end that is open toward the outside,
   wherein a cross-section through the cavity (5) perpendicular to the axis of the earplug has an approximately cross-shaped configuration formed by two intersecting channels.

2. The hearing protection earplug according to claim 1, wherein an outer contour of the cavity (5) is designed rounded in cross-section.

3. The hearing protection earplug according to claim 2, wherein a longitudinal cavity (6) extends inward in the axial direction of the main body from the cross-shaped cavity (5) at the intersection of the two channels.

4. The hearing protection earplug according to claim 1, wherein each of the two intersecting channels is concave shaped downward from the top end of the earplug.

5. The hearing protection earplug according to claim 3, wherein each of the intersecting channels taper inward from the top end of the earplug.

* * * * *